(12) United States Patent
Bonrath et al.

(10) Patent No.: US 8,546,621 B2
(45) Date of Patent: Oct. 1, 2013

(54) PROCESS FOR THE MANUFACTURE OF 3,7-DIMETHYL-1-OCTEN-3-OL

(75) Inventors: Werner Bonrath, Freiburg (DE); Johannes Tschumi, Baltschieder (CH); Jonathan Medlock, Rheinfelden (CH)

(73) Assignee: DSM IP Assets B.V., Heerlen (NL)

( * ) Notice: Subject to any disclaimer, the term of this patent is extended or adjusted under 35 U.S.C. 154(b) by 47 days.

(21) Appl. No.: 13/216,657

(22) Filed: Aug. 24, 2011

(65) Prior Publication Data

US 2012/0053353 A1 Mar. 1, 2012

Related U.S. Application Data

(60) Provisional application No. 61/376,390, filed on Aug. 24, 2010.

(51) Int. Cl.
*C07C 29/14* (2006.01)
*C07C 29/38* (2006.01)
*C07D 311/74* (2006.01)

(52) U.S. Cl.
USPC ............ 568/880; 568/881; 549/410; 549/411

(58) Field of Classification Search
USPC .......................... 568/880, 881; 549/410, 411
See application file for complete search history.

(56) References Cited

U.S. PATENT DOCUMENTS

| 2,780,658 | A | * | 2/1957 | Surmatis ....................... 570/217 |
| 2,783,257 | A | * | 2/1957 | Surmatis et al. .............. 554/115 |
| 6,232,506 | B1 | * | 5/2001 | Kido et al. .................... 568/390 |

FOREIGN PATENT DOCUMENTS

GB 788301 * 12/1957

OTHER PUBLICATIONS

Bonrath et al. Catalytic processes in vitamins synthesis and production. Applied Catalysis A: General, 2005, vol. 280, pp. 55-73.*

* cited by examiner

*Primary Examiner* — Sikarl Witherspoon
(74) *Attorney, Agent, or Firm* — Nixon & Vanderhye P.C.

(57) ABSTRACT

The present invention is directed to a process for the manufacture of 3,7-dimethyl-1-octen-3-ol comprising the following steps:

a) hydrogenation of 6-methyl-5-hepten-2-on to 6-methyl-2-heptanon in the presence of hydrogen and a palladium containing catalyst on a carrier selected from the group consisting of carbon, calcium carbonate and aluminum oxide.

b) reaction of 6-methyl-2-heptanon with acetylene to 3,7-dimethyl-1-octin-3-ol in the presence of ammonia and potassium hydroxide and in the absence of any additional organic solvent;

c) hydrogenation of 3,7-dimethyl-1-octin-3-ol to 3,7-dimethyl-1-octen-3-ol in the presence of hydrogen and a palladium containing catalyst on a carrier selected from the group consisting of calcium carbonate, aluminum oxide, silica, porous glass, carbon or graphite, and barium sulphate, with the proviso that the catalyst additionally contains lead when the carrier is calcium carbonate.

The present invention is further directed to a process for the manufacture of isophytol and vitamin E, where a thus produced 3,7-dimethyl-1-octen-3-ol is used as starting material.

17 Claims, 1 Drawing Sheet

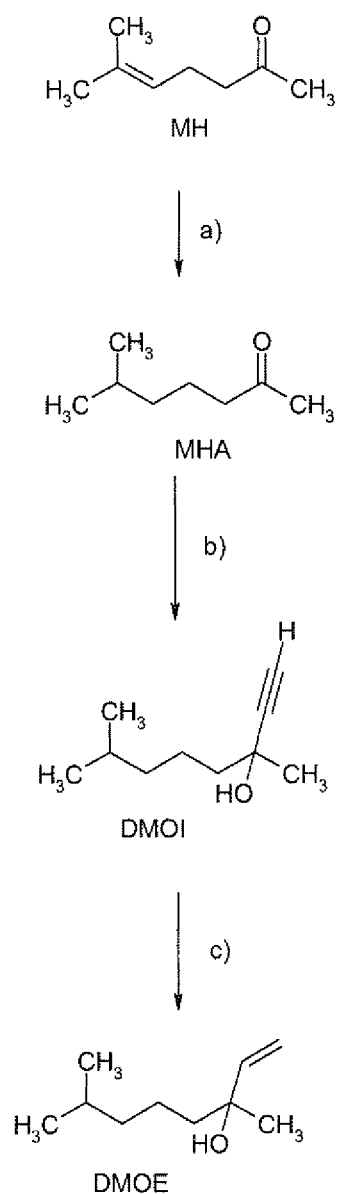

PROCESS FOR THE MANUFACTURE OF 3,7-DIMETHYL-1-OCTEN-3-OL

This application claims the benefit of U.S. Provisional No. 61/376,390, filed 24 Aug. 2010, the entire contents of which are hereby incorporated by reference.

FIELD

According to the process of the present invention 6-methyl-5-hepten-2-on (MH) is hydrogenated to 6-methyl-2-heptanone (MHA) (step a), which is then reacted with acetylene to 3,7-dimethyl-1-octin-3-ol (DMOI) (step b). DMOI is then hydrogenated to 3,7-dimethyl-1-octen-3-ol (DMOE, step c).

BACKGROUND AND SUMMARY

MH itself can be prepared by reaction of isopropenyl methyl ether with 2-methyl-3-buten-2-ol as described by G. Saucy and R. Marbet in Helv. Chim. Acta 1967, 50, 2091-2095.

DMOE as well as tetrahydrolinalool (THLL, 3,7-dimethyl-octan-3-ol) are base products for the flavour and fragrance industry. DMOE, a colourless to pale yellow liquid, has a rose odour and is used in a variety of perfumery applications. It is seen as an alternative to geraniol.

DMOE and THLL are furthermore possible intermediates for isophytol (see e.g. P. Karrer, K. S. Yap, Helv. Chim. Acta 1940, 23, 581), which may be used to manufacture vitamin E (see Ullmann's Encyclopedia of Industrial Chemistry, Editors: Barbara Elvers, Stephen Hawkins, $5^{th}$ completely revised edition, VCH Verlagsgesellschaft mbH, D-69451 Weinheim, 1996, Volume A27 (Thor to Vita), Chapter 4.11.2-4.11.5, page 484-488; especially Chapter 4.11.2 (page 484-485)).

6,10-dimethyl-5-undecen-2-one may be manufactured starting from DMOE according to processes known to the person skilled in the art like e.g. described in U.S. Pat. No. 2,783,257 (see scheme in column 1) and DE-AS 1 193 490 (see example 10). 6,10-Dimethyl-5-undecen-2-one may then be hydrogenated to obtain hexahydropseudoionone (HPI) (see U.S. Pat. No. 2,783,257: column 2, line 58-64), which may be further reacted to (iso)phytol according to processes as e.g. disclosed in Appl. Catal. 2005, 280, 55-73 and Catal. Today 2007, 121, 45-57.

Processes for the manufacture of THLL and DMOE are already known:

P. Karrer and K. S. Yap (Helv. Chim. Acta 1940, 23, 581-584.) describe a procedure for the synthesis of THLL starting from MH. The MH reduction was carried out in the presence of a Pt catalyst, yields were not given. The resulting methylheptanone (MHA) was ethynylated using ethyne and sodium amide. 3,7-Dimethyl-octin-1-3-ol was catalytically reduced in presence of a Pt catalyst. The disadvantage of the procedure is that stoichiometric amounts of the ethynylation agent are used, the hydrogenations are performed with an expensive catalyst, no yields are given (the analysis is not discussed), the reactions are carried out in solvents, and low yields are obtained if we assume that 20 g of MH give 8 g of THLL, based on the experimental procedures reported. The THLL obtained is used for the synthesis of isophytol.

According to U.S. Pat. No. 2,780,658 DMOE (named as 1,5-dimethyl-1-vinyl-1-hexanol) is synthesized starting from MHA which is ethynylated in presence of sodium in liquid ammonia followed by Lindlar hydrogenation in the presence of a catalyst which is Pd/Pb on $CaCO_3$. The hydrogenation was carried out in petroleum ether at 20-30° C. For the hydrogenation of 308 g of the starting material 20 g of the catalyst (s/c≈15) were required.

A similar procedure was claimed in GB 788,301. MHA was ethynylated in ether in presence of ammonia using sodium and ethyne followed by Lindlar hydrogenation in ligroin as solvent. The ethynylation was described to proceed in 82.2% yield.

I. N. Nazarov et al. described in Seriya Khimicheskaya 1957, 1267-1270 and in Zhurnal Obshchei Khimii 1958, 28, 1444-1448 the semi hydrogenation of alkynols in presence of Pd on $CaCO_3$. MHA was ethynylated in 87% yield in presence of solid KOH at 0-20° C. at 5-8 atmospheres, followed by hydrogenation (90%), no conditions were given.

A. Other et al. described in Helv. Chim. Acta 1959, 42, 2577-2584 the Pd/$CaCO_3$ (5% Pd loading) catalyzed hydrogenation of MH to MHA at 34 atm pressure, followed by sodium acetylide treatment to give the corresponding alkynol and Lindlar hydrogenation to DMOE (named as dihydrolinalool).

F. J. Bröcker et al. claimed the preparation and application of hydrogenation catalysts. In EP-A 412 415 the preparation of a Pd catalyst on a support by metal vapour deposition was claimed (300-800° C.), and especially the hydrogenation of 3,7-dimethyl-oct-1-in-3-ol (named as hydro-dehydrolinalool (HDHL)) to DMOE (named as hydro-linalool (HLIN)) was demonstrated (examples 2 and 3: 100% conversion, 99.3%-99.5% selectivity).

EP-A 754 664 describes the partial hydrogenation of alkynes using a solid-bed catalyst as described in EP-A 412 415, whereby the Lindlar hydrogenation was carried out in presence of CO (10-180 ppm).

In EP-A 1 110 932 the above applications are combined and more examples are presented. A similar procedure of alkyne hydrogenation in presence of CO was carried out.

EP-A 816 321 claimed the synthesis of MHA by aldol reaction of acetone and isovaleraldehyde in presence of hydrogen and a conventional hydrogenation catalyst at 15-150° C. and 1-100 bar, (example 3: Pd/C). For the ethynylation of MHA standard protocols were used (example 3, step c, 2 hours, 4-6° C., KOH in water, ammonia). Solvents like NMP, DMSO, and DMF had to be used. These solvents are difficult to separate from the product, (and) especially they could have a negative impact on flavour and fragrance applications. The Lindlar hydrogenation was carried out in a solvent, e.g. hexane, heptane, at 1-130° C. and at 1-50 bar. The preferred catalyst was Pd on $CaCO_3$ (selectivity 95-96%, conversion 97.3-99.7%). In the examples (step 3c, page 20) the Lindlar hydrogenation was carried out in hexane.

The object of the present invention was to provide a process which may be used for the industrial production of DMOE, i.e. a process which is economic. Furthermore, the process according to the present invention should not have the disadvantages of the processes of the prior art.

A preferred object of the present invention was also to achieve a selectivity >90% at a conversion of >95%.

BRIEF DESCRIPTION OF DRAWING

FIG. 1 depicts a reaction scheme wherein 6-methyl-5-hepten-2-on (MH) is hydrogenated to 6-methyl-2-heptanone (MHA) (step a), which is then reacted with acetylene to 3,7-dimethyl-1-octin-3-ol (DMOI) (step b), with DMOI then being hydrogenated to 3,7-dimethyl-1-octen-3-ol (DMOE, step c).

DETAILED DESCRIPTION

The present invention is directed to a process for the manufacture of 3,7-dimethyl-1-octen-3-ol comprising the following steps:
a) hydrogenation of 6-methyl-5-hepten-2-on to 6-methyl-2-heptanon in the presence of hydrogen and a palladium containing catalyst on a carrier selected from the group consisting of carbon, calcium carbonate and aluminum oxide.
b) reaction of 6-methyl-2-heptanon with acetylene to 3,7-dimethyl-1-octin-3-ol in the presence of ammonia and potassium hydroxide and in the absence of any additional organic solvent;
c) hydrogenation of 3,7-dimethyl-1-octin-3-ol to 3,7-dimethyl-1-octen-3-ol in the presence of hydrogen and a palladium containing catalyst on a carrier selected from the group consisting of calcium carbonate, aluminum oxide, silica, porous glass, carbon or graphite, and barium sulphate, with the proviso that the catalyst additionally contains lead when the carrier is calcium carbonate.

Big advantages of the process of the present invention are that the same catalyst as used in step a) may be used in step c), and that steps a) and c) may be performed without the use of an organic solvent such as petroleum ether, ligroin, hexane and heptane.

The single steps are described in more detail in the following.

Step a)

Preferably step a) is performed in the absence of any organic solvent, i.e. that no organic solvent is added to MH or the reaction mixture used in step a). This encompasses also the case that minor amounts of solvent may be present as "impurity" of the MH used.

Preferably the catalyst used in step a) is the same catalyst as used in step c). More preferably this catalyst has a Pd content, based on the total weight of the catalyst, of 1-10, preferred 2.5-8 more preferred, especially preferred 3-7 weight-% Pd. This catalyst is even more preferably Pd on aluminum oxide.

If the catalyst is Pd on aluminum oxide, it preferably has a BET surface area in the range of 50 to 500 m$^2$/g, more preferably it has a BET surface area in the range of 80 to 300 m$^2$/g, most preferably it is an egg-shell catalyst.

An "egg-shell" catalyst in the context of the present invention is a catalyst where the catalytically active metal (Pd) has a non-uniform distribution on the support and is located mainly on the shell of such catalyst.

If the catalyst is Pd on carbon, it preferably has a BET surface area in the range of 800 to 1500 m$^2$/g, more preferably it has a BET surface area in the range of 900-1200 m$^2$/g. Even more preferably 50% of the catalyst also have a size ≤20-50 μm (i.e. the so-called particle size D50≤20-50 μm). Most preferably the bulk density is in the range of 100 to 500 g/L, more preferably in the range of 200 to 300 g/L.

If the catalyst is Pd on CaCO$_3$, it preferably has a BET surface area in the range of 5 to 15 m$^2$/g, more preferably it has a BET surface area in the range of 7 to 10 m$^2$/g. Most preferably 50% of the particles of this catalyst also have a size ≤3-30 μm (i.e. the so-called particle size D50 ≤3-30 μm).

Even more preferably pulverous catalysts including egg-shell catalysts are used. These can be separated easily after the reaction from the reaction mixture by filtration or centrifugation. Furthermore, these catalysts can be recycled and used several times.

Preferably step a) is carried out at a temperature in the range of 20 to 100° C., more preferably at a temperature in the range of 25 to 80° C.

Preferably step a) is carried out at a pressure in the range of 1.1 bar to 15 bar, more preferably at a pressure in the range of 1.5 to 6 bar, even more preferably at a pressure in the range of 1.8 to 4 bar.

Preferably the amount in weight-% of catalyst used in step a) is in the range of 1:50 to 1:5000, more preferably in the range of 1:100 to 1:2500, even more preferably in the range of 1:250 to 1:1000, based on the amount of 6-methyl-5-hepten-2-on in weight-%.

Preferred embodiments of the present invention are also embodiments where several preferred embodiments of step a) as listed above are combined.

Step b)

Preferably the molar ratio of 6-methyl-2-heptanon to acetylene in step b) is in the range of 1:1 to 1:2, more preferably in the range of 1:1.01 to 1:1.5.

Preferably the molar ratio of 6-methyl-2-heptanon to potassium hydroxide in step b) is in the range of 30:1 to 250:1, more preferably in the range of 40:1 to 100:1.

Preferably the molar ratio of 6-methyl-2-heptanon to ammonia in step b) is in the range of 1:15 to 1:50, more preferably in the range of 1:20 to 1:30.

Preferably step b) is carried out at a temperature in the range of −10° C. to 25° C., more preferably at a temperature in the range of 0 to 20° C. The pressure used is preferably in the range of 5 to 25 bar, more preferably in the range of 10 to 20 bar.

Preferred embodiments of the present invention are also embodiments where several preferred embodiments of step b) as listed above are combined.

Step c)

Preferably step c) is performed in the absence of any organic solvent, i.e. that no organic solvent is added to DMOI or the reaction mixture used in step c). This encompasses also the case that minor amounts of solvent may be present as "impurity" of the DMOI used.

Preferably the catalyst used in step c) is a palladium containing catalyst on a carrier selected from the group consisting of calcium carbonate, aluminum oxide, silica, porous glass (especially TRISOPERL®), with the proviso that the catalyst additionally contains lead when the carrier is calcium carbonate.

Preferably the catalyst used in step c) has an amount of palladium in the range of 1 to 10 weight-%, more preferably in the range of 1 to 5 weight-%, based on the total weight of the catalyst, if the carrier is aluminum oxide, silica, porous glass, carbon or graphite and barium sulphate.

A preferred catalyst used in step c) is palladium on calcium carbonate, wherein lead is present. Preferably this catalyst has an amount of lead in the range of 0 to 9 weight-%, more preferably in the range of 1 to 5 weight-%, based on the total weight of the catalyst. The amount of palladium of this catalyst is preferably in the range of 1 to 10 weight-%, more preferably in the range of 3 to 8 weight-%, even more preferably in the range of 5 to 7 weight-%, based on the total weight of the catalyst, If the catalyst is Pd+Pb on CaCO$_3$, it preferably has a BET surface area in the range of 2 to 15 m$^2$/g, more preferably it has a BET surface area in the range of 5 to 15 m$^2$/g, even more preferably it has a BET surface area in the range of 7 to 10 m$^2$/g. Most preferably 50% of the particles of this catalyst also have a size ≤2 to 50 μm (i.e. the so-called particle size D50≤3-30μm), preferably ≤2 to 30μm, more preferably ≤3 to 10 μm.

Most preferably, however, the catalyst used in step c) is the same catalyst as used in step a). This catalyst is more preferably Pd on aluminum oxide.

If the catalyst is Pd on aluminum oxide or silica or any mixture thereof it preferably has a BET surface area in the range of 50 to 500 m$^2$/g, more preferably it has a BET surface area in the range of 80 to 300 m$^2$/g, most preferably it is an egg-shell catalyst.

Preferably step c) is carried out at a temperature in the range of 10° C. to 100° C., more preferably at a temperature in the range of 15 to 60° C.

Preferably step c) is carried out at a pressure in the range of 1.1 bar to 15 bar, more preferably at a pressure in the range of 1.5 to 6 bar, even more preferably at a pressure in the range of 1.8 to 4 bar.

Preferably the amount in weight-% of the catalyst used in step c) is in the range of 1:50 to 1:5000, more preferably in the range of 1:100 to 1:2500, even more preferably in the range of 1:250 to 1:1000, based on the amount of 3,7-dimethyl-1-octin-3-ol in weight-%.

Preferred embodiments of the present invention are also embodiments where several preferred embodiments of step c) as listed above are combined.

Further preferred embodiments of the present invention are embodiments where one or more of the preferred embodiments of step a) and/or step b) and/or step c) as listed above are combined.

The present invention is not only directed to the synthesis of DMOE, but also to the synthesis of (iso)phytol (derivatives) and vitamin E (acetate), especially to a process for the manufacture of isophytol comprising the following steps
preparing DMOE according to the process of the present invention;
preparing 6,10-dimethyl-5-undecen-2-one starting from a thus prepared DMOE;
hydrogenating a thus prepared 6,10-dimethyl-5-undecen-2-one to obtain hexahydropseudoionone;
preparing (iso)phytol or derivatives thereof from a thus prepared hexahydro-pseudoionone.

as well as to a process for the manufacture of vitamin E (acetate) comprising the following steps
reacting 2,3,6-trimethylhydroquinone (TMHQ) or 2,3,6-trimethylhydroquinone-1-acetate (TMHQA) with (iso) phytol or derivatives thereof or any mixture thereof to obtain vitamin E or its acetate.

Derivatives of phytol and isophytol are especially those as disclosed in EP-A 694-541: page 4, line 39 to page 5, line 14 and in WO 2005/121115: page 4, line 11 to 19 with n=3, whose content is incorporated herein by reference.

The invention is now further illustrated in the following non-limiting examples.

EXAMPLES

In the examples the following catalysts were used:
a 5% Pd/C catalyst which was oxidized and dried and is e.g. commercially available from Evonik under the tradename "5% Pd/C E 101 O/D" ("catalyst A");
a 5% Pd/C catalyst with a BET surface area of 1000 m$^2$/g, a bulk density in the range of 200 and 300 g/L and the following particle size distribution: 10% of the particles ≤6 μm, 50% of the particles ≤28 μm, and 90% of the particles ≤79 μm, which is e.g. commercially available from Evonik under the tradename "5% Pd/C E 101 N/D" ("catalyst B");
a 5% Pd/C catalyst with a specific surface area of 1000 m$^2$/g, a volume of the micropores of 0.30 ml/g, a volume of the mesopores of 0.40 ml/g, a volume of the macropores of 0.40 ml/g, a bulk density in the range of 200 and 300 g/L; a volume of the pores of 1.10 ml/g and a mixed metal localisation, which is e.g. commercially available from Evonik under the tradename "10% Pd/C Evonik E 101 N/D" ("catalyst C");
a 5% Pd/CaCO$_3$ egg-shell catalyst with a BET surface area of 8 m$^2$/g, a bulk density of 0.37 kg/l, and whereby 50% of the particles have a size ≤5 μm which is e.g. commercially available from Evonik under the tradename "5% Pd/CaCO$_3$ Evonik E 407 R/D" ("catalyst D");
a 5% Pd/Al$_2$O$_3$ egg-shell catalyst with a surface area in the range of 50-300 m$^2$/g, a bulk density in the range of 0.5-1 kg/l and a pore volume in the range of 0.1 to 0.5 ml/g. Such a catalyst with a surface area of 93 m$^2$/g, a bulk density of 0.8 kg/l and a pore volume of 0.3 ml/g is e.g. commercially available from Evonik under the tradename "5% Pd/Al$_2$O$_3$ Evonik E 213 XR/D" ("catalyst E");
a 5% Pd/Al$_2$O$_3$ catalyst as e.g. commercially available from Engelhard under the tradename "5% Pd/Al$_2$O$_3$ Engelhard Lot. 09784" ("catalyst F");
a 5% Pt/C catalyst with a BET area in the range of 500 to 1000 m$^2$/g, whereby 50% of the particles have a size ≤21 μm. Such a catalyst with a BET area of 800 m$^2$/g, whereby 50% of the particles have a size ≤21 μm, is e.g. commercially available from Engelhard under the tradename "5% Pt/C Engelhard Lot. 07608" ("catalyst G");
a 5% Rh/C catalyst which is e.g. commercially available from Evonik under the tradename "5% Rh/C, Evonik G 101 XB/D" ("catalyst H");
a catalyst with 5% Pd and 3.5% Pb supported on CaCO$_3$ with a BET area in the range of 5 to 15 m$^2$/g and a bulk density in the range of 0.2 to 1.0 kg/l, whereby 50% of the particles have a size ≤2 to 10 μm. Such a catalyst with a BET area of 8 m$^2$/g and a bulk density of 0.37 kg/l, whereby 50% of the particles have a size ≤5 μm is e.g. commercially available from Evonik under the tradename "5% Pd 3.5% Pb CaCO$_3$ Evonik CE 407 R/D" ("catalyst I");
a catalyst with 5% Pd and 1% Pb supported on CaCO$_3$ as e.g. commercially available from J&M under the tradename "5% Pd 1% Pb CaCO$_3$ J&M A-304050-5" ("catalyst J");
a catalyst with 7% Pd and 9% Pb supported on CaCO$_3$ as e.g. commercially available from Evonik under the tradename "7% Pd 9% Pb CaCO$_3$ Evonik CE 407 R/D" ("catalyst K");
an egg-shell catalyst with 5% Pd and 2.5% Pb supported on CaCO$_3$ with a BET area in the range of 5 to 15 m$^2$/g, whereby 50% of the particles have a size ≤20 to 50 μm which may be manufactured according to processes known to the person skilled in the art ("catalyst L");
a catalyst with 5% Pd and 5% Pb supported on CaCO$_3$ with a BET area in the range of 2 to 15 m$^2$/g, a bulk density in the range of 0.2 to 1.0 kg/l and a pore volume in the range of 1.0 to 2.0 ml/g, whereby the particles have a size ≤100 μm. Such a catalyst with a BET area of 5 m$^2$/g, a bulk density of 0.45 kg/L and a pore volume of 1.6 ml/g, whereby the particles have a size ≤100 μm is e.g. commercially available from Heraeus under the tradename "5% Pd 5% Pb CaCO$_3$ Heraeus" ("catalyst M");
a 5% Pd/SiO$_2$ catalyst as e.g. commercially available from Engelhard under the tradename "5% Pd/SiO$_2$ Engelhard A 596033" ("catalyst N");

a 1% Pd/C catalyst as e.g. commercially available from Evonik under the tradename "1% Pd/charcoal Degussa E 101 N/D" ("catalyst O");

a 5% Pd/graphite reduced catalyst as e.g. commercially available from Engelhard under the tradename "5% Pd/graphite Engelhard" ("catalyst P");

a 5% Pd/BaSO$_4$ catalyst as e.g. commercially available from Evonik under the tradename "5% Pd/BaSO$_4$ Evonik E 50 N/D" ("catalyst Q");

a 3.7 weight-% Pd/Al$_2$O$_3$ catalyst, whereby the Pd is in the form of nano-particles as e.g. commercially available from SDC under the tradename "3.7% Pd/Al$_2$O$_3$SDC Nanokat" ("catalyst R");

a 1% Pd/TP catalyst ("catalyst S") whose manufacture is described below.

1% Pd/TP was Manufactured as Follows:

21 mg Pd(OAc)$_2$ (0.09 mmol) were suspended in 50 mL of dichloromethane. 1 g of TRISOPERL® were added and the solvent was removed (bath temperature: 40° C./pressure: 950 mbara). The carrier doped with Pd(OAc)$_2$ was calcinated for 2 hours at 300° C. in an oven (pre-heating of the oven for 20 minutes for 1000 W to 300° C.). The loading of the catalyst on the carrier was then ca. 1 weight-% Pd, i.e. 10 mg of Pd on 1 g of carrier. TRISOPERL® by the Schuller GmbH, Wertheim/Germany, is a porous Silica glass with an average particle size in the range of 100 to 200 μm, an average pore size of 54.47 nm, a specific surface of 93.72 m$^2$/g and an average pore volume of 1255.5 mm$^3$/g.

Step a

Examples 1 to 7

A 125 mL-autoclave (Hastelloy) was charged with 30 g of MH with a purity of 96.7% and the catalyst as given in table 1. The amount of catalyst was 33.3 mg in all examples. The mixture was heated to 60° C. and hydrogen was added at 2 bar. After reaction, when no up-take of hydrogen was observed any more, the mixture was cooled to 20° C., the catalyst separated by filtration and the mixture analyzed by gas chromatography.

TABLE 1

Synthesis of MHA by use of various catalysts

| Example | Catalyst | Reaction time [h:min] | Conversion [mol %] | Selectivity [mol %] | Yield [mol %] |
|---|---|---|---|---|---|
| 1 | A: 5% Pd/C | 11:40 | 99.2 | 97.9 | 97.1 |
| 2 | B: 5% Pd/C | 21:00 | 98.6 | 87.7 | 86.5 |
| 3 | D: 5% Pd/CaCO$_3$ | 24:00 | 95.4 | 97.6 | 93.2 |
| 4 | C: 10% Pd/C | 43:34 | 94.3 | 97.8 | 92.3 |
| 5 | E: 5% Pd/Al$_2$O$_3$ | 66:00 | 100.0 | 97.3 | 97.3 |
| 6 | F: 5% Pd/Al$_2$O$_3$ | 24:00 | 80.5 | 89.6 | 72.1 |
| 7 | R: 3.7% Pd/Al$_2$O$_3$ | 39:46 | 63.4 | 88.6 | 56.2 |

The catalysts used in examples 5 and 6 are pulverous catalysts.

Step a

Examples 8 to 11

Example 2 was repeated at various temperatures and/or pressures. The results are shown in table 2. The catalyst used was catalyst B (5% Pd/C).

TABLE 2

Synthesis of MHA at various temperatures and/or pressures

| Example | Amount of catalyst [mg] | Temperature [° C.] | Pressure [bar] | Reaction time [h:min] | Conversion [mol %] | Selectivity [mol %] | Yield [mol %] |
|---|---|---|---|---|---|---|---|
| 2 | 33.3 | 60 | 2 | 21:00 | 98.6 | 87.7 | 86.5 |
| 8 | 33.3 | 30 | 2 | 24:00 | 99.8 | 93.5 | 93.4 |
| 9 | 33.3 | 80 | 2 | 24:00 | 62.1 | 80.0 | 49.7 |
| 10 | 33.3 | 60 | 10 | 24:00 | 99.8 | 94.2 | 94.0 |
| 11 | 33.3 | 30 | 10 | 20:00 | 99.9 | 91.9 | 91.8 |

Step a

Comparison Examples 1 and 2

Example 1 was repeated but different metals used as catalyst. The results are summarized in table 3. As the results show platinum on carbon as well as rhodium on carbon give less conversion and less selectivity, thus also less yield on the desired product, than palladium on carbon.

TABLE 3

Synthesis of MHA by use of different metals on carbon as catalyst

| Example | Catalyst | Amount of catalyst [mg] | Reaction time [h:min] | Conversion [mol %] | Selectivity [mol %] | Yield [mol %] |
|---|---|---|---|---|---|---|
| 1 | A: 5% Pd/C | 33.3 | 11:40 | 99.2 | 97.9 | 97.1 |
| Comparison example 1 | G: 5% Pt/C | 33.3 | 24:00 | 39.4 | 74.2 | 29.2 |
| Comparison example 2 | H: 5% Rh/C | 33.3 | 24:00 | 54.0 | 85.8 | 46.3 |

Step b

Example 12

In a 2 liter autoclave under nitrogen, 860 g of liquid ammonia were added to 319.4 g of methylheptanone. The mixture was cooled down to 15° C. (pressure: 9.8 bar). Then acetylene was added until a pressure of 12 bar was achieved. Then 6.4 g of an aqueous 45 weight-% KOH solution was added. The reactor pressure of 12 bar was maintained by continued addition of acetylene. In total 66.7 g of acetylene were used. At the end of the reaction (after ca. 3.3 hours) 10 g of an aqueous 90 weight-% acetic acid solution were added, the pressure was relieved whereby the main part of ammonia was evaporated. By heating to 40° C. the remaining ammonia was removed. Then the reaction mixture was washed twice with 100 ml of de-ionized water, twice with 100 ml of an aqueous 8 weight-% sulphuric acid solution and again twice with 100 ml of de-ionized water.

The experiment was repeated three times. The conversion was 97.3% in average, the yield was 96.0% in average before washing and 95.3% afterwards, and the selectivity was 98.7%.

Step c

Examples 13 to 30

A 150 mL-autoclave (Hastelloy) was charged with 40 g of DMOI with a purity of 99.8% and the amount and catalyst as given in table 4. 4.7 mg of the modifier 2,2' ethylene-dithiodiethanol were added. The mixture was heated to 30° C. and hydrogen was added at 2 bar. After reaction, when no up-take of hydrogen was observed any more, the mixture was cooled to 20° C., the catalyst separated by filtration and the mixture analyzed by gas chromatography.

TABLE 4

Synthesis of DMOE by use of various catalysts

| Example | Catalyst | Amount of catalyst [mg] | Reaction time [h:min] | Conversion [mol %] | Selectivity [mol %] | Yield [mol %] |
|---|---|---|---|---|---|---|
| 13 | I: 5% Pd 3.5% Pb CaCO$_3$ | 34.8 | 16:00 | 99.5 | 92.3 | 91.9 |
| 14 | I: 5% Pd 3.5% Pb CaCO$_3$ | 34.8 | 05:49 | 100.0 | 94.2 | 94.2 |
| 15 | I: 5% Pd 3.5% Pb CaCO$_3$ | 34.8 | 04:44 | 99.5 | 95.4 | 94.1 |
| 16 | I: 5% Pd 3.5% Pb CaCO$_3$ | 34.8 | 04:42 | 100.0 | 95.2 | 95.2 |
| 17 | J: 5% Pd 1% Pb CaCO$_3$ | 34.8 | 03:49 | 98.5 | 92.7 | 93.9 |
| 18 | J: 5% Pd 1% Pb CaCO$_3$ | 24.8 | 03:51 | 100.0 | 92.8 | 92.8 |
| 19 | K: 7% Pd 9% Pb CaCO$_3$ | 34.8 | 04:20 | 99.4 | 94.1 | 95.4 |
| 20 | L: 5% Pd 2.5% Pb CaCO$_3$ | 34.8 | 06:25 | 99.5 | 95.3 | 96.5 |
| 21 | M: 5% Pd 5% Pb CaCO$_3$ | 34.8 | 08:00 | 99.4 | 95.5 | 96.8 |
| 22 | S: 1% Pd/Trisoperl | 180.0 | 04:06 | 98.9 | 91.0 | 88.5 |
| 23 | S: 1% Pd/Trisoperl | 120.0 | 04:37 | 98.3 | 91.7 | 87.7 |
| 24 | E: 5% Pd/Al$_2$O$_3$ | 34.8 | 04:01 | 98.6 | 90.9 | 92.1 |
| 25 | E: 5% Pd/Al$_2$O$_3$ | 20.0 | 04:31 | 98.6 | 90.6 | 91.8 |
| 26 | N: 5% Pd/SiO2 | 34.8 | 23:03 | 100.0 | 81.9 | 83.0 |
| 27 | O: 1% Pd/charcoal | 34.8 | 16:52 | 98.4 | 88.4 | 84.7 |
| 28 | P: 5% Pd/graphite | 34.8 | 21:00 | 97.6 | 88.4 | 82.9 |
| 29 | F: 5% Pd/Al$_2$O$_3$ | 34.8 | 20:30 | 98.8 | 89.4 | 86.6 |
| 30 | Q: 5% Pd/BaSO$_4$ | 69.6 | 5:00 | 98.5 | 90.4 | 86.8 |

Step c

Examples 31 to 36

Example 13 was repeated at different temperature and/or pressure. The results are shown in table 5. The catalyst used was catalyst I (5% Pd 3.5% Pb on CaCO$_3$).

TABLE 5

Synthesis of DMOE at different temperature and/or pressure

| Example | Amount of catalyst [mg] | Temperature [° C.] | Pressure [bar] | Reaction time [h:min] | Conversion [mol %] | Selectivity [mol %] | Yield [mol %] |
|---|---|---|---|---|---|---|---|
| 13 | 34.8 | 30 | 2 | 16:00 | 99.5 | 92.3 | 91.9 |
| 31 | 34.8 | 30 | 2 | 25:00 | 100.0 | 93.1 | 93.1 |
| 32 | 34.8 | 30 | 2 | 6:30 | 99.9 | 94.6 | 94.2 |
| 33 | 34.8 | 40 | 2 | 21:30 | 100.0 | 91.4 | 91.4 |
| 34 | 34.8 | 40 | 2 | 10:45 | 100.0 | 91.7 | 91.7 |
| 35 | 34.8 | 20 | 2 | 22:00 | 100.0 | 93.8 | 93.8 |
| 36 | 34.8 | 30 | 10 | 22:00 | 100.0 | 90.0 | 90.0 |

Step c

Examples 37 and 38

Example 13 was repeated with different modifiers. The reactions were all performed at 2 bar and 30° C. The results are shown in table 6.

TABLE 6

Synthesis of DMOE, whereby the catalysts were modified with different modifiers

| Example | Modifier | Amount of modifier [mg] | Reaction time [h:min] | Conversion [mol %] | Selectivity [mol %] | Yield [mol %] |
|---|---|---|---|---|---|---|
| 13 | 2,2'ethylene-dithiodiethanol | 4.7 | 16:00 | 99.5 | 92.3 | 91.9 |
| 37 | Thiophene | 4.7 | 8:10 | 100.0 | 89.7 | 89.7 |
| 38 | Pyridine | 4.7 | 5:30 | 100.0 | 89.2 | 89.2 |

Step c

Example 39 and Comparison Examples 40 to 41

Example 13 was repeated with different metal catalysts, but no modifier was used. The reactions were all performed at 2 bar and 30° C. The results are shown in table 7.

TABLE 7

Synthesis of DMOE with different catalysts, whereby no modifier was used

| Example | Catalyst | Amount of catalyst [mg] | Reaction time [h:min] | Conversion [mol %] | Selectivity [mol %] | Yield [mol %] |
|---|---|---|---|---|---|---|
| 39 | I: 5% Pd 3.5% Pb CaCO$_3$ | 34.8 | 5:38 | 100.0 | 91.2 | 91.2 |
| Comparison example 40 | G: 5% Pt/C | 34.8 | 19:00 | 89.4 | 51.4 | 37.3 |
| Comparison example 41 | H: 5% Rh/C | 34.8 | 24:00 | 71.8 | 60.8 | 16.4 |

The invention claimed is:
1. A process for the manufacture of 3,7-dimethyl-1-octen-3-ol comprising the following steps:
   a) hydrogenating 6-methyl-5-hepten-2-on to 6-methyl-2-heptanon in the presence of hydrogen and a palladium- containing catalyst on a carrier selected from the group consisting of carbon, calcium carbonate and aluminum oxide;
b) reacting the 6-methyl-2-heptanon obtained in step a) with acetylene in the presence of ammonia and potassium hydroxide and in the absence of any additional organic solvent to obtain 3,7-dimethyl-1-octin-3-ol; and
c) hydrogenating the 3,7-dimethyl-1-octin-3-ol obtained in step b) to 3,7-dimethyl-1-octen-3-ol in the presence of hydrogen and a palladium-containing catalyst on a carrier selected from the group consisting of calcium carbonate, aluminum oxide, silica, porous glass, carbon or graphite, and barium sulphate, with the proviso that the catalyst additionally contains lead when the carrier is calcium carbonate, wherein the palladium-containing catalyst used in step a) is the same palladium-containing catalyst as used in step c).

2. The process according to claim 1, wherein the palladium-containing catalyst is Pd on aluminum oxide.

3. The process according to claim 1, wherein the palladium-containing catalyst used in steps a) and c) is palladium on calcium carbonate, and wherein lead is present.

4. The process according to claim 1, wherein step a) is carried out at a temperature in the range of 40° C. to 80° C.

5. The process according to claim 1, wherein step a) is carried out at a pressure in the range of 1.1 bar to 10 bar.

6. The process according to claim 1, wherein the amount in weight-% of catalyst used in step a) is in the range of 1:50 to 1:5000, based on the amount of 6-methyl-5-hepten-2-on in weight-%.

7. The process according to claim 1, wherein the molar ratio of 6-methyl-2-heptanon to acetylene in step b) is in the range of 1:1 to 1:2.

8. The process according to claim 1, wherein the molar ratio of 6-methyl-2-heptanon to potassium hydroxide in step b) is in the range of 30:1 to 250:1.

9. The process according to claim 1, wherein the molar ratio of 6-methyl-2-heptanon to ammonia in step b) is in the range of 1:15 to 1:50.

10. The process according to claim 1, wherein step b) is carried out at a temperature in the range of −10° C. to 25° C. and at a pressure in the range of 5 to 25.

11. The process according to claim 1, wherein step c) is carried out at a temperature in the range of room temperature (20° C.) to 100° C.

12. The process according to claim 1, wherein step c) is carried out at a pressure in the range of 1.1 bar to 10 bar.

13. The process according to claim 1, wherein the amount in weight-% of the catalyst used in step c) is in the range of 1:50 to 1:5000, based on the amount of 3,7-dimethyl-1-octin-3-ol in weight-%.

14. The process according to claim 1, wherein the catalyst used in steps a) and c) has an amount of palladium in the range of 1 to 10 weight-%, based on the total weight of the catalyst.

15. The process according to claim 3, wherein the catalyst used in steps a) and c) has an amount of lead in the range of 0 to 9 weight-%, based on the total weight of the catalyst.

16. A process for the manufacture of phytol, isophytol or derivatives thereof comprising the following steps:
(i) preparing 3,7-dimethyl-1-octen-3-ol (DMOE) according to claim 1;
(ii) preparing 6,10-dimethyl-5-undecen-2-one starting from a thus prepared DMOE;
(iii) hydrogenating a thus prepared 6,10-dimethyl-5-undecen-2-one to obtain hexahydropseudoionone; and
(iv) preparing phytol, isophytol or derivatives thereof from a thus prepared hexahydropseudoionone.

17. A process for the manufacture of vitamin E or its acetate comprising the following step:
reacting 2,3,6-trimethylhydroquinone (TMHQ) or 2,3,6-trimethylhydroquinone-1-acetate (TMHQA) with phytol, isophytol or derivatives thereof or any mixture thereof as manufactured according to claim 16 to obtain vitamin E or its acetate.

* * * * *